(12) United States Patent
Barker et al.

(10) Patent No.: US 8,899,834 B2
(45) Date of Patent: Dec. 2, 2014

(54) PIVOT JOINT BRAKES FOR X-RAY POSITIONING SYSTEM

(75) Inventors: David Ellis Barker, Salt Lake City, UT (US); John Matthew Simmons, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 409 days.

(21) Appl. No.: 13/449,777

(22) Filed: Apr. 18, 2012

(65) Prior Publication Data

US 2013/0279663 A1  Oct. 24, 2013

(51) Int. Cl.
*G21K 5/10* (2006.01)
*H05G 1/02* (2006.01)
*A61B 6/00* (2006.01)

(52) U.S. Cl.
USPC ........... 378/197; 378/198; 378/193; 378/196; 250/582; 250/370.09; 250/522.1

(58) Field of Classification Search
USPC ............. 378/193, 196–198, 210; 250/370.09, 250/395, 492.1, 522.1, 526, 580, 582–584
See application file for complete search history.

(56) References Cited

U.S. PATENT DOCUMENTS

| | | | |
|---|---|---|---|
| 4,104,525 A | 8/1978 | Franke | |
| 4,856,036 A | 8/1989 | Malcolm et al. | |
| 5,077,771 A | 12/1991 | Skillicorn et al. | |
| 5,627,873 A | 5/1997 | Hanover et al. | |
| 5,631,943 A | 5/1997 | Miles | |
| 6,007,243 A | 12/1999 | Ergun et al. | |
| 6,113,265 A * | 9/2000 | Babler | 378/197 |
| 6,203,196 B1 * | 3/2001 | Meyer et al. | 378/197 |
| 6,234,672 B1 | 5/2001 | Tomasetti et al. | |
| 6,236,712 B1 | 5/2001 | Tomasetti et al. | |
| 6,256,374 B1 | 7/2001 | Tomasetti et al. | |
| 7,530,739 B2 * | 5/2009 | Lurz et al. | 378/198 |
| 7,607,832 B2 * | 10/2009 | Jensen et al. | 378/197 |
| 8,708,561 B2 * | 4/2014 | Eaves | 378/198 |
| 2010/0239073 A1 * | 9/2010 | Eaves | 378/198 |
| 2012/0300909 A1 * | 11/2012 | Simmons et al. | 378/194 |

* cited by examiner

*Primary Examiner* — Bernard E Souw
(74) *Attorney, Agent, or Firm* — Kenneth E. Horton; Kirton McConkie

(57) ABSTRACT

Systems and methods for braking and releasing one or more pivot joints used in an X-ray positioning device are described. The systems and methods use a support arm that extends between a main assembly of the x-ray positioning device and an X-ray imaging assembly with an X-ray source and an X-ray detector that are disposed nearly opposite to each other. The support arm includes one or more pivot joints (such as horizontal, lateral, and/or orbital pivot joints) that allow the imaging assembly to move with respect to the main assembly. The pivot joints can each be connected to an automated braking system that is capable of selectively locking and unlocking a corresponding pivot joint, as indicated by a user-controlled switching mechanism. The braking systems containing multiple pivot joints can be individually controlled by separate switching mechanisms or simultaneously controlled by a single switching mechanism. Other embodiments are described.

20 Claims, 4 Drawing Sheets

PIVOT JOINT BRAKES FOR X-RAY POSITIONING SYSTEM

FIELD

This application relates generally to X-ray equipment. More specifically, this application relates to systems and methods for braking and releasing one or more pivot joints used in an X-ray positioning system.

BACKGROUND

A typical X-ray imaging system comprises an X-ray source and an X-ray detector. X-rays emitted from the X-ray source can impinge on the X-ray detector and provide an X-ray image of the object or objects that are placed between the X-ray source and the detector. In one type of X-ray imaging system, a fluoroscopic imaging system, the X-ray detector is often an image intensifier or, more recently, a flat panel digital detector.

In addition to the X-ray source and the X-ray detector, the typical fluoroscopic imaging system comprises a main assembly, a movable support assembly, and a gantry or X-ray imaging assembly. The main assembly is coupled to the movable support assembly, and the support assembly supports the movable gantry or imaging assembly. In mobile imaging systems, the main assembly typically includes wheels for moving and/or positioning the imaging system.

Fluoroscopic imaging systems can be either fixed or mobile. For instance, fixed fluoroscopic imaging systems often include a gantry that is secured to a floor, wall, column, or ceiling. Additionally, mobile fluoroscopic imaging systems are movable so that they can be used in a variety of clinical environments, such as different departments of a medical facility. The gantry or imaging assembly of a mobile fluoroscopic imaging system may include a C-arm (i.e., mini C-arm), O-arm, L-arm, or another imaging assembly.

In some configurations, a C-arm assembly of a fluoroscopic imaging system remains stationary relative to a subject for single angle imaging. In other configurations, the C-arm assembly moves relative to the subject so as to acquire images from multiple angles. In some cases, a movable support assembly supporting the C-arm assembly includes one or more pivot joints that allow the C-arm to be repositioned with respect to the subject being X-rayed.

SUMMARY

This application describes systems and methods for braking and releasing one or more pivot joints used in an X-ray positioning device. The systems and methods use a support arm that extends between a main assembly of the x-ray positioning device and an X-ray imaging assembly with an X-ray source and an X-ray detector that are disposed nearly opposite to each other. The support arm includes one or more pivot joints (such as horizontal, lateral, and/or orbital pivot joints) that allow the imaging assembly to move with respect to the main assembly. The pivot joints can each be connected to an automated braking system that is capable of selectively locking and unlocking a corresponding pivot joint, as indicated by a user-controlled switching mechanism. The braking systems containing multiple pivot joints can be individually controlled by separate switching mechanisms or simultaneously controlled by a single switching mechanism.

BRIEF DESCRIPTION OF THE DRAWINGS

The following description can be better understood in light of the Figures, in which.

Figure 1:
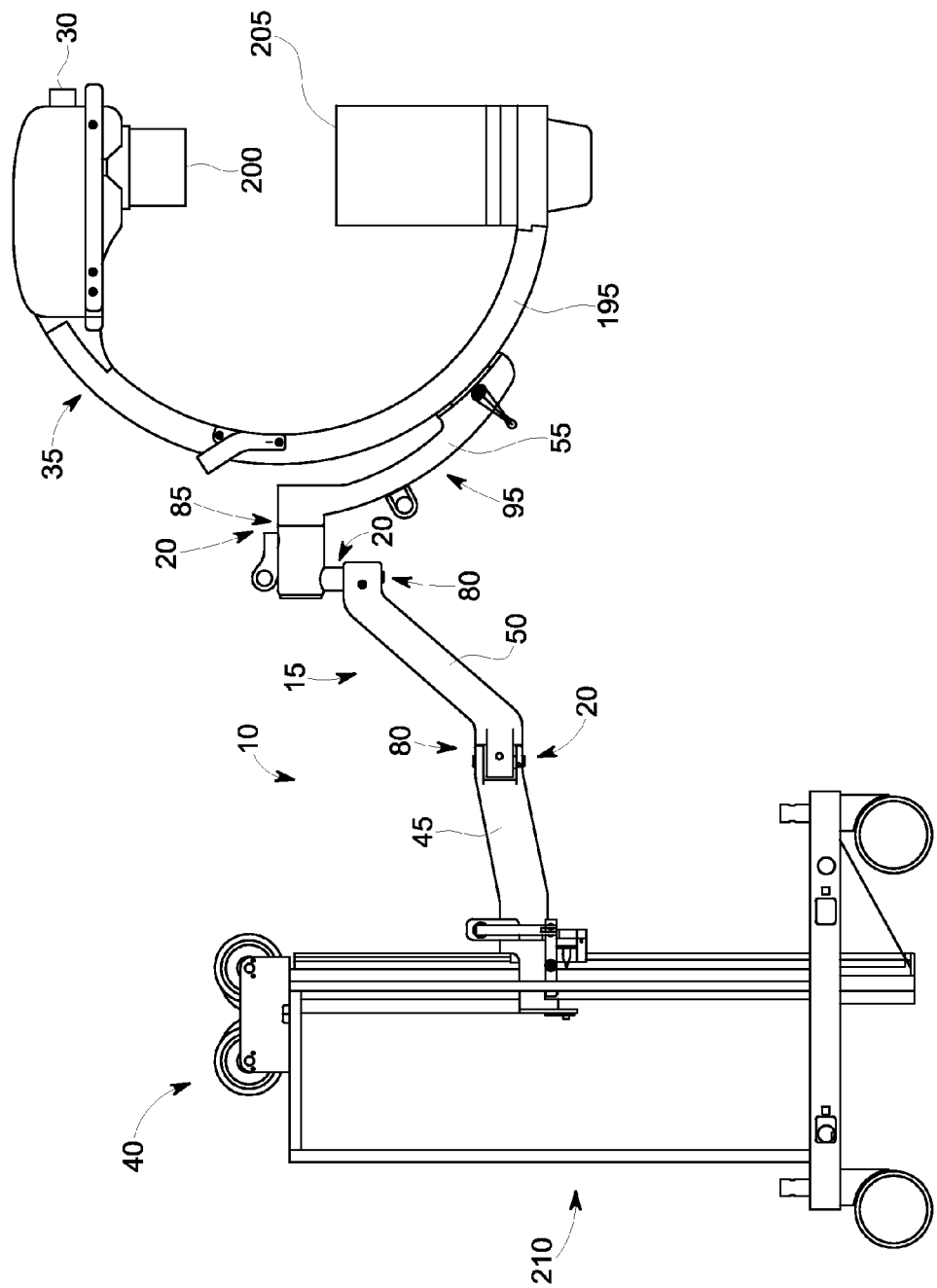
FIG. 1 shows a side view of some embodiments of an X-ray positioning device comprising a support arm that is connected to an X-ray imaging assembly through a rear imaging assembly capture mechanism.

The Figures illustrate specific aspects of systems and methods for braking and releasing one or more pivot joints used in an X-ray positioning device. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described systems and methods for braking and releasing one or more pivot joints used in an X-ray positioning system, as well as the associated methods of making and using such systems, can be implemented and used without employing these specific details. Indeed, the described systems and methods can be placed into practice by modifying the described systems and methods and can be used in conjunction with any other apparatus and techniques conventionally used in the industry. For example, while the description below focuses on systems and methods for braking and releasing one or more pivot joints used in an X-ray positioning device comprising an X-ray imaging assembly (i.e., a mini C-arm), they can be used with virtually any other suitable type of X-ray equipment in which an X-ray imaging assembly can be repositioned through the movement of one or more pivot joints. Some examples of such X-ray imaging assemblies include a standard C-arm, a compact style C-arm, a dental X-ray gun, and a non-circular arm.

Some conventional X-ray positioning systems contain one or more pivot joints that are used to position an X-ray imaging assembly. They also requires a user to manually lock (e.g., by manually twisting a knob) a pivot joint to retain the imaging assembly in a desired location. Such systems can require a relatively large amount of physical effort, can be time consuming to operate, and otherwise be inconvenient to use. The pivot joints in some of the conventional X-ray positioning systems are often factory set with a built-in tension, which only allows a user to reposition the X-ray imaging assembly when the user applies enough force to overcome (or break away from) the pre-set tension.

The systems and methods described herein, however, contain one or more pivot joints that automatically lock and/or unlock the pivot joints' movement as directed by one or more user-controlled switching mechanisms that operate easily with a minimum amount of force. The Figures show some embodiments of the described systems for braking and releasing one or more pivot joints used in an X-ray positioning system. These systems can comprise any suitable component that allows a user reposition an X-ray imaging assembly (or imaging assembly) by selectively locking and/or unlocking one or more automatic braking systems on corresponding pivot joints. FIG. 1 shows some embodiments in which such systems comprise an X-imaging device 10 that includes one or more movable support assemblies (or support arms 15), pivot joints 20, pivot joint breaking systems 25 (not shown in FIG. 1), user-controlled switching mechanisms 30, imaging assemblies 35, and main assemblies 40.

Figure 2:
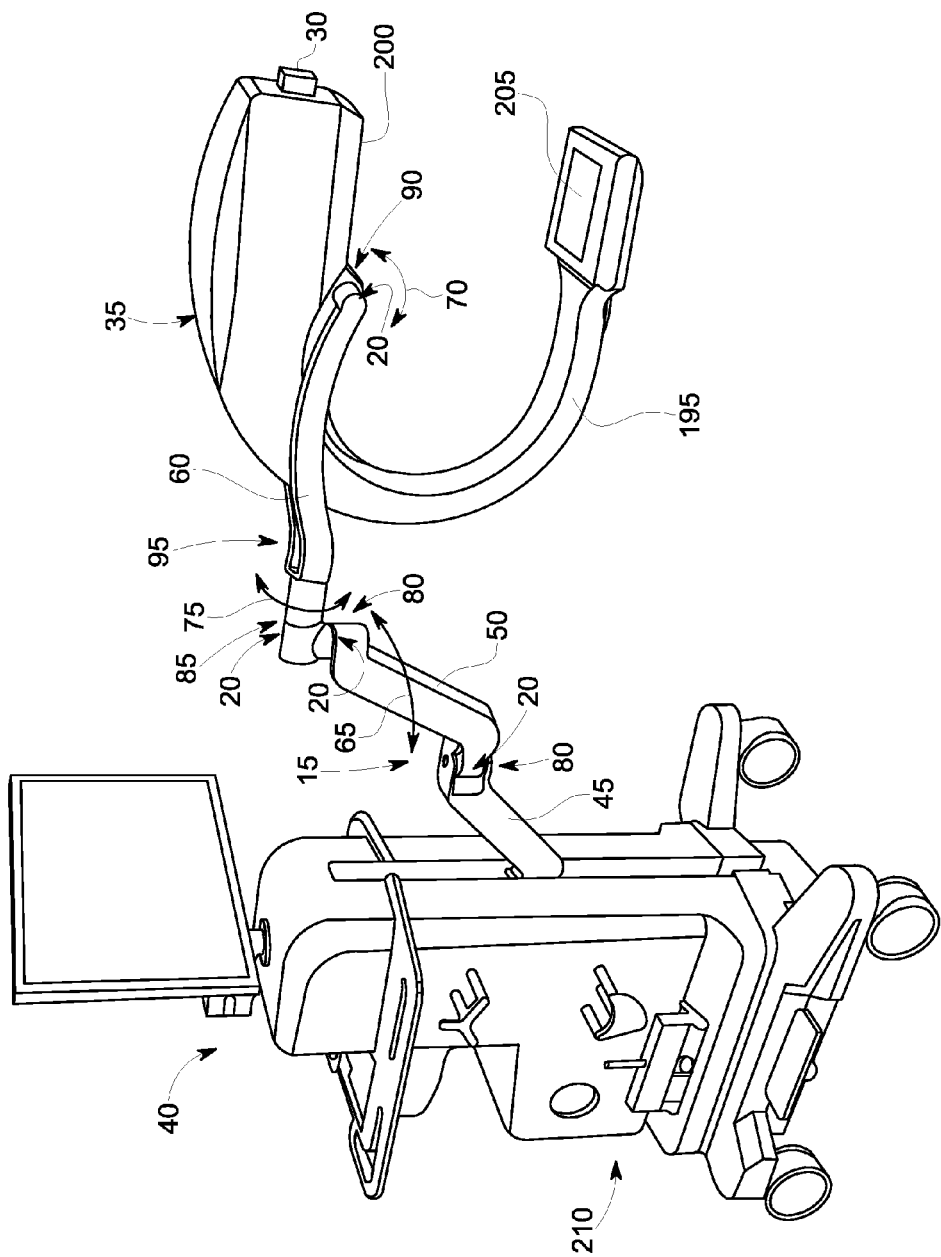
FIG. 2 shows a side perspective view of some embodiments of the X-ray positioning device, wherein the imaging assembly attaches to the support arm through an orbital pivot joint.

The support arm can be configured to movably support the imaging assembly 35 with respect to the main assembly 40. In some configurations, the support arm can have any number of elongated supports and imaging assembly connectors (e.g., imaging assembly support forks, side/rear imaging assembly capture mechanism, etc.). For example, the support arm can have 1, 2, 3, 4, 5, or even more elongated supports and/or imaging assembly connectors. FIG. 1 shows some embodiments in which the support arm 15 comprises a first elongated support 45, a second elongated support 50, and rear imaging assembly capture mechanism 55. FIG. 2 shows other embodiments in which the support arm 15 comprises two elongated supports (45 and 50) and an imaging assembly support fork 60.

The support arm 15 can comprise any suitable type of pivot joint 20 that allows the imaging assembly 35 to be moved with respect to the main assembly 40. Some examples of suitable pivot joints include horizontal pivot joints, orbital pivot joints, lateral pivot joints, vertical pivot joints, ball pivot joints, and any other joints that allow the imaging assembly 35 to be pivoted from one position to another. A horizontal pivot joint comprises a joint that allows imaging assembly to pivot horizontally through an arc of motion (e.g., as illustrated by arrow 65 in FIG. 2). An orbital pivot joint comprises a joint that provides the imaging assembly with an axis of orbital rotation about the joint (e.g., as illustrated by arrow 70 in FIG. 2). A lateral pivot joint comprises a joint that allows the imaging assembly to be laterally rotated clockwise and/or counter-clockwise (e.g., as illustrated by arrow 75 in FIG. 2). A vertical pivot joint comprises a joint that allows the imaging assembly to pivot vertically through an arc of motion. FIG. 2 shows some embodiments in which the X-ray imaging device 10 comprises two horizontal pivot joints 80, a lateral pivot joint 85, and an orbital pivot joint 90.

The pivot joints 20 can be disposed in any location on the X-ray imaging device 10 that allows the imaging assembly 35 to be pivoted from one position to another. In some configurations, the X-ray imaging device can comprise a pivot joint between the first elongated support 45 and the main assembly 40, between any elongated support elements (e.g., between the first 45 and second 50 elements), between an elongated support (e.g., the second elongated support 50) and the imaging assembly connector 95, and/or between the support arm 15 (e.g., the support fork 60) and the imaging assembly. FIG. 2 shows some embodiments in which the support arm 15 comprises a pivot joint 20 between the first 45 and second 50 elongated supports (e.g., horizontal pivot 80), between the second elongated support 50 and the imaging assembly connector 95 (e.g., horizontal pivot joint 80 and lateral pivot joint 85), and between the imaging assembly connector (e.g., the support fork 60) and the imaging assembly 35 (e.g., orbital pivot joint 90).

The automated braking system 25 can comprise any braking mechanism capable of allowing a user to selectively lock a pivot joint in a desired position and/or unlock the joint from that position. In some embodiments, the terms lock, locking, and the like may refer to a position of the braking system involving an increased brake tension on the joint 20 that either prevents the joint from moving or that requires more force to move the joint than would be required if the brake were not in the locked position (e.g., if the brake were unlocked). Some examples of the braking system 25 include systems that comprise a shaft clamp that extends around a portion of pivot shaft (e.g., 105 in FIG. 3) in the pivot joint 20, a drum brake having a brake pad disposed within an interior cavity of the pivot shaft, a disc brake that corresponds to a disc extending radially from the pivot shaft, a pawl that can be inserted into or otherwise be used to stop and/or release movement of the pivot shaft, and/or any other automated braking mechanisms that a user can use to selectively lock and unlock the joint.

Figure 3:
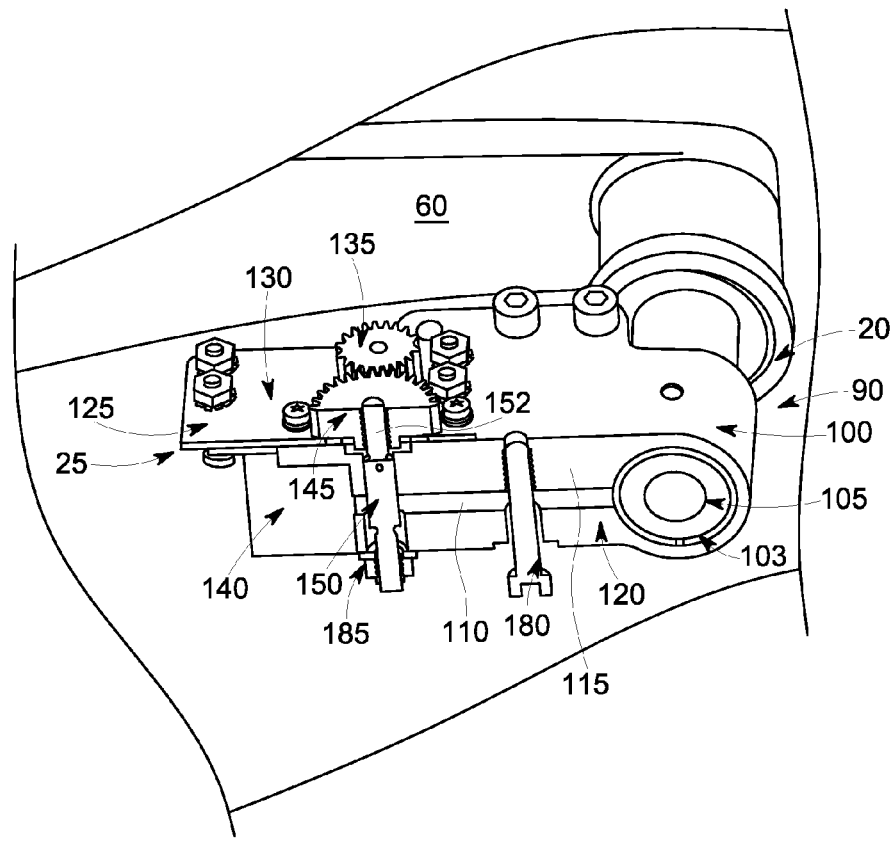
FIG. 3 shows a perspective, partial cut-away view of some embodiments of a pivot joint braking system comprising a motorized actuator.

In some embodiments, however, the braking system comprises a shaft clamp. As illustrated in FIG. 3, the braking system 25 comprises a shaft clamp 100 that extends around a portion of the pivot shaft 105 in the pivot joint 20, along with an optional bushing 103. The clamp 100 can define a gap 110 between a first 115 and a second 120 side of the shaft clamp 100. The braking system 25 also comprises an actuator mechanism 125 (or actuator) that is configured to selectively lock the joint 20 by decreasing the width of the gap 110 and unlock the joint by increasing the width of the gap. The actuator 125 can be configured to selectively increase and/or decrease the width of the gap between the clamp's first 115 and second 120 side. Some examples of actuator mechanisms include a motorized actuator, an electromagnetic actuator, a camming device, a hydraulic actuator, a solenoid actuator, and/or a servomechanism.

In some embodiments, the actuator 125 comprises a motorized actuator. In these embodiments, the motorized actuator can configured to selectively increase and decrease the width of the gap 110 between the clamp's first 115 and second 120 sides. Indeed, FIG. 3 shows some embodiments in which the motorized actuator 130 comprises a motor-output gear 135 that is driven by a motor 140 which, in turn, spins a gear nut 145 that tightens or loosens on a threaded shaft 150 that extends between the clamp's first 115 and second 120 sides. The threaded shaft 150 can contain a threaded lead 152 with a sufficiently low number of threads at an angle that allows the gear nut 145 to loosen on the threaded shaft when the actuator 125 is de-energized. In other embodiments, however, the lead on the threaded shaft has a sufficient number of threads with a gradual enough slope that the gear nut remains in place on the threaded shaft, even when the actuator is completely de-energized. Accordingly, the braking system 25 can remain locked without requiring electrical power. Thus, some embodiments of the braking system can be relatively power efficient and remain locked during a loss of power to the X-ray imaging device 10.

Figure 4:
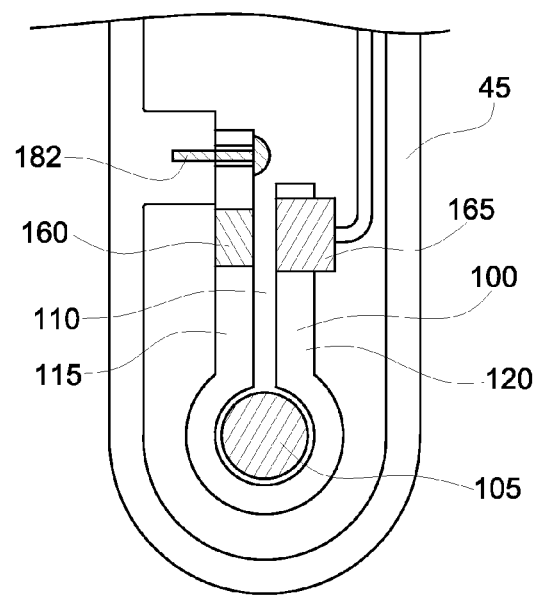
FIGS. 4 and 5 show different views of some embodiments of the pivot joint breaking system comprising an electromagnetic actuator.
Figure 5:
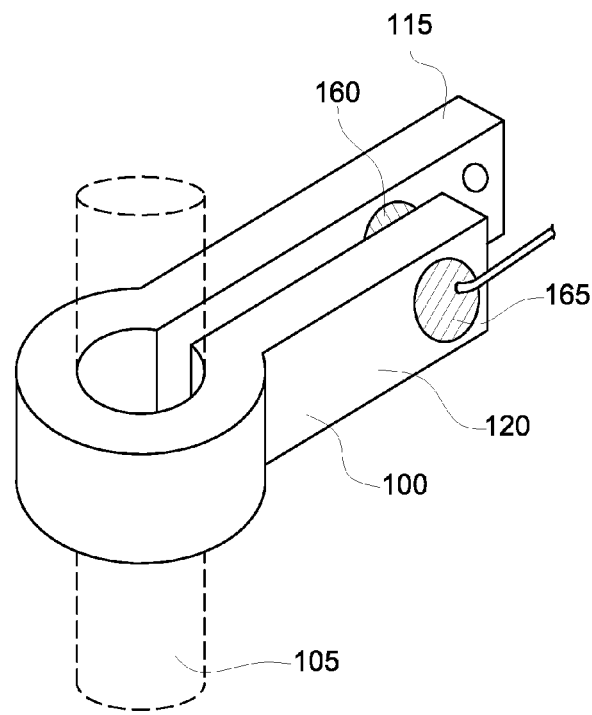

In some embodiments, the actuator 125 can comprise an electromagnetic actuator, as shown in FIGS. 4 and 5. In these embodiments, an electromagnetic actuator 155 comprises a permanent magnet 160 at the first side 115 of the clamp 100 and an electromagnet 165 at the second side 120 of the clamp. In such embodiments, when the electromagnet is actuated (e.g., a user switches it on), the electromagnet pulls on the permanent magnet and tightens the clamp to the locked position.

Figure 6:
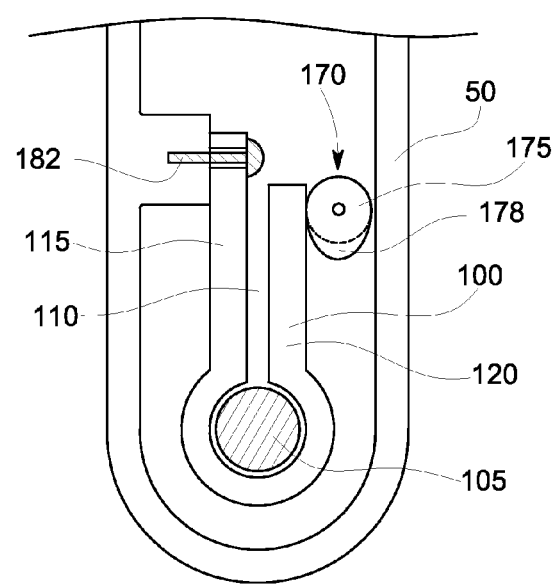
FIG. 6 shows a top schematic view of some embodiments of the pivot joint breaking system comprising a camming device.

In some embodiments, the actuator 125 can comprise a camming mechanism that allows it to lock and unlock the braking mechanism 25. In these embodiments, FIG. 6 shows that the camming mechanism 170 comprises a motor-driven cam 175. The cam of the camming mechanism can rotate so that the cam's eccentric portion 178 contacts the clamp 100. The cam locks the pivot joint 20 by forcing one side of the clamp (e.g., second side 120) towards the other side (e.g., first side 115 anchored by fastener 182). When the cam's eccentric portion moves out of contact with the side of clamp, the clamp is able to relax and unlock by increasing the width of the clamp's gap 110.

In some embodiments, the braking system 25 is adjustable so that the friction created by the braking system on the pivot joint 20 (e.g., on the pivot shaft 105) in the locked and/or unlocked positions can be adjusted. The braking system can be adjusted in any suitable manner, including through the use of one or more bolts. FIG. 3 shows some embodiments in which the braking system 25 comprises a brake unlock adjust screw 180 that allows the shaft clamp 100 to be tightened or loosened to define the minimum friction that is applied by the clamp to the shaft 105 when the brake is in the unlocked position. FIG. 3 also shows some embodiments where the braking system 25 comprises a brake lock adjust nut 185 that can be tightened or loosened on the threaded shaft 150 to increase or decrease the friction between the clamp 100 and the shaft 105 when the braking system is locked. Thus, the braking system can be adjusted to be clutched so that the braking system can be adjusted to be overcome by applying additional torque on the joint to get the shaft to slip in the clamp.

Since the braking system 25 comprises an actuator 125, a user can use the actuator mechanism to move the braking system 25 between a locked and an unlocked position using a switching mechanism. The switching mechanism can be an electrical switching mechanism and/or a manual switching mechanism. With an electrical switching mechanism, the actuator can be switched by any suitable user-controlled (or other) electrical switching mechanism, which can be located in any suitable position. Some examples of suitable user-controlled switching mechanisms 30 include, one or more tactile-membrane switches, toggle switches, buttons, touch-screen interfaces, electrical adjustment knobs, sliding switches, adjustable switches, dome switches, lever switches, proximity switches, pressure switches, speed switches, temperature switches, tactile switches, relays, momentary-type switches, motion detection switches, tuners, joysticks, and/or other switches that can be used to control the actuator 125. By way of illustration, FIGS. 1 and 2 show embodiments in which the switching mechanism 30 comprises a button 190.

In some embodiments, the braking system 25 of each pivot joint 20 can be controlled by a separate switching mechanism. In other embodiments, the braking systems of any number or combination of the pivot joints are controlled by a single switching mechanism. For example, the braking system of the horizontal joints 80, the lateral joint 85, the orbital joint 90, and/or any other movable part can be moved between a locked and an unlocked position through the use of the same switching mechanism (e.g., switch 30) simultaneously or otherwise.

The switching mechanism 30 can allow the actuator 125 to tighten or loosen the braking system 25 by any suitable amount when the braking system is moved between the locked and the unlocked position. For example, the switching mechanism can be configured to have the braking system tighten or loosen to provide a pre-set friction. In another configuration, however, the switching mechanism (e.g., a momentary-type switch) allows the user to tighten or loosen the braking system to provide a desired level of friction (e.g., within the limits set by brake unlock adjustment screw 180 and brake lock adjustment nut 185, where applicable).

Turning to the imaging assembly, the X-ray imaging device 10 can comprise any imaging assembly that allows the device to take X-ray images of a portion of a patient's body. For example, the imaging assembly can comprise a mini C-arm, a standard C-arm, an O-arm, and L-arm, a compact style C-arm, and/or a non-circular arm. By way of illustration, FIGS. 1 and 2 show some embodiments in which the imaging assembly 35 comprises a mini C-arm 195.

The imaging assembly 35 can be configured so that X-ray images of a portion of a patient's body can be taken. For example, FIG. 1 shows some embodiments in which the imaging assembly 35 comprises an X-ray source 200 and detector 205. The X-ray source can comprise any source that generates and emits X-rays, including a standard X-ray source, a rotating anode X-ray source, a stationary or fixed anode X-ray source, a solid state X-ray emission source, and/or a fluoroscopic X-ray source. The X-ray detector can comprise any detector that detects X-rays (i.e., an image intensifier and/or a digital flat panel detector).

The support arm 15 can be connected to any main assembly 40 capable of holding the imaging assembly 35 at a desired vertical and/or horizontal position. In some configurations, the support arm can connected to a fixed support structure, such as a wall, a column, a floor, a shelf, a cabinet, a stationary frame, a ceiling, a door, a sliding structure, a bed, a gurney, a rail, and/or any other support structure (or structures) that are not intended to be easily moved and repositioned around a patient.

In other configurations, though, the support arm 15 is connected to a movable main assembly 40. In such configurations, the movable main assembly can be configured to move across a floor while supporting the imaging assembly. Thus, the movable support structure can comprise one or more wheels, shelves, handles, monitors, computers, stabilizing members, limbs, legs, struts, cables, and/or weights (to prevent the weight of the imaging assembly and/or any other component from tipping the movable support structure). FIG. 1 shows some embodiments in which the movable main assembly 40 comprises a wheeled structure 210 that supports the support arm 15 and the imaging assembly 35.

The described systems and methods can be modified. For example, the pivot joints 20 can comprise one or multiple automated brake systems 25. In another example, the pivot joints can also comprises one or more manual brake systems, which can be used on the same or different joints than the automated brake systems.

The described pivoting X-ray devices 10 can be made in any suitable manner that forms the structures described. For example, the pivoting X-ray devices can be formed through a process involving molding, extruding, casting, cutting, stamping, bending, drilling, bonding, welding, mechanically connecting, frictionally connecting, and/or any other process.

The pivoting X-ray devices 10 can also be used for any X-ray imaging process. By way of example, a user can position the imaging assembly 35 by moving the arm about one or more pivot joints 20. Additionally, the user can selectively lock the imaging assembly (e.g., the pivot joints) at any suitable location and/or unlock the arm in any suitable manner (e.g., via a user-controlled switching mechanism 30).

The pivoting X-ray devices 10 may have several useful features. First, unlike some conventional pivot joint brakes that require a user to manually tighten and loosen each pivot joint individually, some of the X-ray devices 10 allow a user to lock and unlock the braking system 25 on one or more pivot joints 30 with a single electronic switching mechanism 30 (e.g., a single switch). Thus, these systems may require less physical effort, be easier to use, be faster to use, and otherwise be more convenient than some conventional systems. Second, unlike some conventional pivot joint brakes that are pre-set to apply a set amount of friction to the joint and which only allow the joint to be moved when tension on the joint exceeds the preset amount of friction (e.g., passive brakes), some of the X-ray devices 10 can allow the joints to be moved with relatively little effort when the joints are in an unlocked position. Third, unlike some conventional passive brakes that tend to allow the support arm 15 to drift as the X-ray device 10 ages, some of the X-ray devices 10 can lock the support arm in place without any drifting. And fourth, unlike some conventional brakes that release when power to the brake is cut, some of the X-ray devices 10 can retain the braking system 25 in the locked position, even when power to the braking system is cut.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A support arm attaching an X-ray imaging assembly to a main assembly, the support arm comprising:
   a first end configured to attach to an X-ray imaging assembly;
   a second end configured to attach to a main assembly; and
   a first pivot joint attached to the support arm between the imaging assembly and the main assembly, wherein the first pivot joint comprises a first automated braking system that selectively locks and unlocks a movement of the first pivot joint by using a first user-controlled switching mechanism.

2. The support arm of claim 1, wherein the pivot joint comprises a horizontal pivot joint.

3. The support arm of claim 1, wherein the pivot joint comprises an orbital pivot joint that provides the imaging assembly with an axis of orbital rotation.

4. The support arm of claim 1, further comprising a second pivot joint with a second automated braking system, wherein the first braking system and the second braking system are controlled by the first switching mechanism.

5. The support arm of claim 1, further comprising a second pivot joint with a second automated braking system, wherein the first braking system is controlled by the first switching mechanism and the second braking system is controlled by a second user-controlled switching mechanism.

6. The support arm of claim 1, wherein the support arm further comprises a first elongated support that attaches to the main assembly and a second elongated support that attaches to the imaging assembly and the first pivot joint comprises a horizontal pivot joint that is disposed between the first and second elongated supports.

7. The support arm of claim 1, wherein the first automated braking system does not require electricity to retain it in a locked position.

8. The support arm of claim 1, wherein the first pivot joint comprises a pivot shaft, the first braking system comprises a shaft clamp extending around a portion of the pivot shaft, the shaft clamp defines a gap between a first and second side of the shaft clamp, and the braking system comprises an actuator to decrease and increase a width of the gap to lock and unlock the first braking system, respectively, when indicated by the first switching mechanism.

9. The support arm of claim 8, wherein the actuator comprises a motorized actuator, a hydraulic actuator, a solenoid actuator, an electromagnetic actuator, a camming device, a servomechanism, or a combination thereof.

10. An X-ray imaging device, comprising:
    a support arm extending between a main assembly and an X-ray imaging assembly, wherein the imaging assembly comprises an X-ray source and an X-ray detector that are disposed at nearly opposing locations of the imaging assembly;
    a first pivot joint attached to the support arm to allow the imaging assembly to move with respect to the main assembly; and
    a first automated braking system that selectively locks and unlocks a movement of the first pivot joint by a first user-controlled switching mechanism.

11. The device of claim 10, wherein the first pivot joint comprises a pivot shaft, the first braking system comprises a shaft clamp extending around a portion of the pivot shaft, the shaft clamp defines a gap between a first and second side of the shaft clamp, and the first braking system comprises an actuator to decrease and increase a width of the gap to lock and unlock the first braking system, respectively, when indicated by the first switching mechanism.

12. The device of claim 10, wherein the pivot joint comprises a horizontal pivot joint.

13. The device of claim 10, wherein the pivot joint comprises a lateral pivot joint.

14. The device of claim 10, wherein the pivot joint comprises an orbital pivot joint that provides the imaging assembly with an axis of orbital rotation.

15. The device of claim 10, further comprising a second pivot joint with a second automated braking system, wherein the first braking system and the second braking system are simultaneously controlled by the first switching mechanism.

16. The device of claim 1, wherein the first braking system does not require electricity to retain it in a locked position.

17. An X-ray imaging device, comprising:
    a support arm extending between a main assembly and an X-ray imaging assembly, wherein the imaging assembly comprises an X-ray source and an X-ray detector that are disposed at nearly opposing locations of the imaging assembly;
    a first pivot joint attached to the support arm to allow the imaging assembly to move with respect to the main assembly; and
    a first automated braking system and a second automated braking system that lock and unlock the first and second pivot joint, respectively, when indicated by a user.

18. The device of claim 17, wherein the first pivot joint comprises a horizontal pivot joint and the second pivot joint comprises an orbital pivot joint.

19. The device of claim 17, wherein the first and second braking systems are controlled by the first user-controlled switching mechanism.

20. The device of claim 17, wherein the first automated braking system is controlled by a first user-controlled switching mechanism and the second braking system is independently controlled by a second user-controlled switching mechanism.

* * * * *